United States Patent [19]
Mann

[11] Patent Number: 5,768,936
[45] Date of Patent: Jun. 23, 1998

[54] ADHESION AND COHESION PAINT TESTING SYSTEM

[76] Inventor: George Mann, 1816 Oak St., Pasadena, Calif. 91030

[21] Appl. No.: 871,507

[22] Filed: Jun. 9, 1997

Related U.S. Application Data

[63] Continuation-in-part of Ser. No. 746,496, Nov. 12, 1996, Pat. No. 5,673,586, which is a continuation-in-part of Ser. No. 184,429, Jan. 21, 1994, Pat. No. 5,575,868, which is a continuation of Ser. No. 910,626, Jul. 8, 1992, Pat. No. 5,265,850.

[51] Int. Cl.$^6$ .................................................. G01N 19/08
[52] U.S. Cl. ....................................................... 73/150 A
[58] Field of Search ............................. 73/826, 827, 834, 73/855, 838, 839, 150 A, 150 R; 156/64, 378; 118/712

[56] References Cited

U.S. PATENT DOCUMENTS

| | | | |
|---|---|---|---|
| 4,393,699 | 7/1983 | Seiler, Jr. ............................. | 73/150 A |
| 4,501,154 | 2/1985 | Mori ....................................... | 73/827 |
| 4,567,758 | 2/1986 | Fisher et al. ......................... | 73/150 A |

*Primary Examiner*—Robert Raevis
*Attorney, Agent, or Firm*—Charles H. Thomas

[57] ABSTRACT

A method and apparatus are provided for testing the adhesive strength of a bond between an adhesive, a coating such as paint, or some other material, and an underlying substrate to which the test substance is bonded. The coating to be tested is applied atop the substrate in a smooth, continuous layer. An aperture is formed through the substrate and the test substance. A thin film patch is positioned atop an area of the test substance directly above the aperture. The film extends beyond the perimeter of the aperture and resides in contact with the test substance. The test substance is scored about the perimeter of the thin film patch. A thin plate which maintains its elastic property with only minor yielding during the test is bonded to the test substance by means of a layer of high-strength adhesive interposed between the plate and the test substance. The adhesive strength of the bond between the plate and the substance being tested must be greater than the bond between the substance being tested and the substrate. The test assembly thereby produced is clamped within a test fixture and pressure is applied through an aperture in the test fixture from the side of the substrate opposite the surface of the substrate to which the test substance is bonded. With increasing pressure the plate is deformed at the aperture through the substrate thereby applying force to the area of the test substance surrounding the thin film patch until the critical pressure is reached and the bond between the test substance and the substrate fails.

20 Claims, 4 Drawing Sheets

ADHESION AND COHESION PAINT TESTING SYSTEM

BACKGROUND OF THE INVENTION

The present invention is a continuation-in-part of U.S. application Ser. No. 08/746,496 filed Nov. 12, 1996, now U.S. Pat. No. 5,673,586, issued Oct. 7, 1997, which is a continuation-in-part of U.S. application Ser. No. 08/184,429 filed Jan. 29, 1994, now U.S. Pat. No. 5,575,868, issued Nov. 19, 1996, which is a continuation of U.S. application Ser. No. 07/910,626, filed Jul. 8, 1992, now U.S. Pat. No. 5,265,850.

This invention was made with government support under grant ECD 9119322 awarded by the National Science Foundation.

1. Field of the Invention

The present invention relates to a testing apparatus and a method for testing the bonding strengths and/or cohesion strengths of coatings and adhesives.

2. Description of the Prior Art

For many years those skilled in the art have attempted to find a suitable method for measuring adhesive strength which would provide results independent of the testing process. One such approach is a so-called "blister" method. In this process a fluid, either gas or liquid, is injected under the coating through a hole in its substrate forcing the coating to lift from the substrate in the form of a blister.

A promising enhancement of the blister technique was described by Dannenberg in 1960 (H. Dannenberg, "Measurement of Adhesion by a Blister Method", J. of Applied Polymer Science, Vol. V, No. 14, pp 125–134 (1961)). However, this process is complex and has not been widely accepted.

In 1977 A. B. Featherston described a further procedure involving the blister method for the evaluation of the adhesive strength of coatings (Optimization of Processing Variables Which Affect Adhesion of Organic Materials, reported in Vought Corporation Document AD-A048467, April 1977). None of the known blister testing methods has been widely accepted.

One of the principal problems associated with the use of the blister method to evaluate the adhesion of a coating is that the film of the coating will often rupture before the coating debonds from the substrate. Also, the varying elasticities of most coatings will cause varying relationships between the height and the diameter of the paint blister formed, thus producing varying test results. Additionally, to determine bonding strength the blister method requires measuring both the elevation of the paint or other coating from the underlying surface to which it is bonded as well as the pressure at which debonding occurs. This results in a complex calculation for materials with a nonlinear stress-strain relationship.

Another limitation common with conventional blister testing methods is that they must be conducted in a laboratory at normal room temperatures and are not suitable for testing at extreme environmental conditions, such as high or low temperatures.

My prior U.S. Pat. No. 5,575,868, issued Nov. 19, 1996, describes certain devices and techniques which solve significant problems previously encountered in ascertaining the bonding strength of coatings and adhesives to underlying substrates. The entirety of the disclosure of my prior U.S. Pat. No. 5,575,868 is incorporated herein by reference.

In addition to the advantages over the prior art provided by the invention of my prior U.S. Pat. No. 5,575,868, I discovered certain additional advantages in a variation of my prior work which is the subject matter of my pending U.S. application Ser. No. 08/746,496, filed Nov. 12, 1996, presently pending. The entirety of the disclosure of my prior U.S. application Ser. No. 08/184,429 is incorporated herein by reference.

While the system of my prior U.S. application Ser. No. 08/184,429 provides remarkably consistent and accurate results for certain test substances, such as adhesives, the results are not as satisfactory for other test substances, such as paint. Now, however, I have discovered a further variation for a test system that provides superb test results for test substances such as paint.

Specifically, in constructing a test device it is advisable to employ a substrate, which takes the form of a rigid structure typically formed of a hard material to which the coating or adhesive to be tested is often applied. Such substrates may take the form of sheets or plates of aluminum, stainless steel, plastics, wood and other rigid materials. In preparing a test device to measure the adhesive strength of a test substance, for example, a coating of paint, it is necessary to introduce a fluid under pressure to a plate bonded to the test substance tending to separate the coating from the substrate.

SUMMARY OF THE INVENTION

According to the present invention there is a fluid passageway through which pressure is provided against the underside of a plate bonded to a test substance. The passageway is most conveniently formed by drilling a hole through the substrate. The substrate is then coated with the test substance. The test substance is thereafter cured or dried. To obtain consistency of results it is important to avoid any irregularities in the demarcation between the area of the coating to be tested and the substrate. Where the substrate is formed of wood, slight splintering can occur around the edges of the aperture when the aperture is drilled through the substrate. If the area of the coating tested extends up to the very edge of the fluid aperture in the substrate, inconsistent results may occur due to irregularities at the circumference of the aperture on the face of the substrate to which the adhesive or coating is applied.

To avoid possible errors in measurement that might otherwise result, the present invention provides a system for eliminating the interface between the coating to be tested at the fluid aperture while still maintaining a consistent, reproducible area within the perimeter of the substrate at which the coating is bonded to the substrate. It is this area about the center which is tested.

In the prior systems of my U.S. Pat. No. 5,575,868 and my prior U.S. application Ser. No. 08/746,496 a consistent, reproducible peripheral area of bonding was provided by creating a consistent, reproducible area of absence of bonding between the test substance, namely the adhesive or coating, and the substrate, at the center of the test device. According to the present invention, however, a reproducible, consistent test area of bonding between the test substance and the substrate is provided by positioning a thin film atop the test substance directly over the aperture and scoring or forming a groove in the test substance about the entire perimeter of the thin film so as to isolate the portion of the test substance within the area encircled by the scoring or the groove from the peripheral area of the test substance that is also bonded to the substrate. Fluid pressure applied through the aperture thereby acts upon the plate which in turn debonds the test substance beyond the perimeter of the thin film, but not upon that portion of the test substance immediately adjacent the aperture in the substrate.

A patch formed of a thin film of known geometric dimensions is positioned atop the test substance and extends beyond the edges of the aperture. The test substance is scored about the entire circumference of the patch, which extends a sufficient distance beyond the aperture to prevent the occurrence of any inconsistent test results that might otherwise occur if the area of the coating on the substrate right up to the edges of the pressure aperture is tested. Preferably, the thin film extends beyond the edges of the aperture at least about 0.625 inches throughout the perimeter of the aperture. Preferably also, the aperture has a circular cross section and the thin film is formed as a circular patch having a diameter of one and a half inches and positioned atop the test substance in coaxial alignment with the fluid aperture.

The use of a thin film cover that extends beyond the perimeter of the aperture has other advantages as well. By utilizing such a cover the need for a temporary plug in the fluid aperture is eliminated. That is, in some of my prior systems a plug was temporarily inserted into the fluid aperture during the time that the adhesive that bonds the plate or membrane to the test substance was applied. The plug prevented the bonding adhesive, the test coating, or both from dripping down into the fluid aperture. By employing a thin film patch according to the present invention, however, no such plug is necessary.

The present invention has other advantages as well. Specifically, the apparatus and method employed allow testing of both cohesive and adhesive failure of a bond between a test substance and a substrate. In testing the strength of a bond for adhesive failure, the specimen is examined following testing to determine whether or not separation of the test substance has occurred at the interface between the test substance, namely between the coating, and the substrate. If the separation that occurs is at the interface between the test substance and the substrate, the critical pressure measured is indicative of the strength of the adhesive bond between the test substance and the substrate. This critical pressure for any particular test substance will vary, depending upon the substrate to which it bonds, since test substances will adhere with greater or lesser tenacity to substrates formed of different materials, or to substrates prepared differently prior to bonding.

On the other hand, failure may occur within the test substance itself. Internal cohesive failure occurs when the layer of the test substance separates laterally within itself in a plane substantially normal to the direction in which the force of separation is applied. That is, in cohesive failure a portion of the test substance, namely the coating being tested, remains attached to the substrate, while another portion of the test substance remains attached to the plate or membrane that is lifted from the substrate by pressure applied through the aperture in the substrate. Separation therefore occurs within the test substance itself, and not at the interface between the test substance and either the substrate or the overlying plate or membrane. In this case the critical pressure creating the failure is indicative of the cohesive strength of the test substance.

Cohesive strength is evaluated within the test substance as the specific work of cohesive failure of the test substance. When cohesive failure occurs internally within the test substance, the substrate employed is not material to the test results as long as the adhesive strength of the bond between the test substance and the substrate exceeds the internal cohesive strength of internal bonding within the substance being tested.

The present invention provides a relatively simple adhesive or cohesive strength testing method and system which provide consistent measurements of bonding strength, which does not require measuring the elevation of the test substance before separation, and which can be conducted in extreme environmental conditions.

The present invention uses increasing pressure against a membrane or plate bonded to a coating to facilitate the determination of the adhesive bond strength between a coating and a substrate to which it is bonded by measuring the pressure required to debond the coating from the substrate. The present invention also facilitates the determination of the internal cohesive strength in the adhesive or coating itself. The adhesive and cohesive strengths may be determined at room temperatures or at extreme temperatures within an environmental chamber.

In one broad aspect the present invention may be considered to be a system for testing the strength of the bond between a test substance and a rigid substrate through which an aperture is defined. The system is comprised of a plate and an overcoat adhesive layer between the plate and the test substance. The overcoat adhesive layer bonds the plate to the test substance with an adhesive strength greater than the strength of the bond between the test substance and the substrate. A thin film is interposed between the test substance and the overcoat adhesive layer directly above the aperture. The thin film extends beyond the perimeter of the aperture. The test substance is scored about the periphery of the thin film. A means is also provided for applying increasing pressure though the aperture in the substrate to debond the test substance from the substrate. In addition, a means is provided for determining the critical pressure required to substantially debond a continuous periphery of an area in the test substance from the substrate, the critical pressure being directly related to the specific work of debonding.

Preferably, the means for determining the critical pressure further comprises means for determining the adhesive strength of the bond between the test substance and the substrate directly from the pressure required to cause substantial bond failure as a function of the specific work of debonding the test substance from the substrate.

In another broad aspect the present invention may be considered to be a system for testing the cohesive strength of a test substance bonded to a rigid substrate through which an aperture is defined. The system is comprised of a plate and an overcoat adhesive layer bonded to that plate and to the test substance. The adhesive strength of the bond between the plate and the test substance is greater than the cohesive strength of the test substance. A thin film over the test substance is interposed between the test substance and the overcoat adhesive layer directly atop the aperture and extending beyond the perimeter of the aperture. A groove is formed in the test substance about the periphery of the thin film to avoid the application of pressure to the portion of the test substance directly beneath the thin film. A means is provided for applying increasing pressure through the aperture in the substrate to cause cohesive failure in the test substance A means is also provided for determining the critical pressure required to cause cohesive failure around a continuous periphery of an area in the test substance, the critical pressure being directly related to the specific work of cohesive failure.

The failure of the test substance may occur as either a failure of the adhesive bond between the test substance and the substrate, or as an internal cohesive failure within the substance being tested itself. In either event the adhesive or cohesive strength is expressed as the specific work of debonding or cohesive failure, and is calculated using the critical pressure and a formula based upon constants inherent to the system. In some embodiments of the invention substrate reinforcements may be utilized and firmly secured to the substrate to prevent errors that might otherwise occur due to deflections in the substrate.

The system of the invention can be used to determine the strength of both adhesive and cohesive bonds holding the test substance to the substrate. When utilized to determine the adhesive strength of the bond between the test substance and the substrate at the interface therebetween, the means for determining the critical pressure is further comprised of means for measuring the pressure at the moment the bond between the test substance and the substrate fails. When the system is utilized to determine the cohesive strength of the test substance, the means for determining the critical pressure is comprised of means for determining the internal cohesive strength of the test substance directly from the pressure required to cause substantial cohesive failure therewithin as a function of the specific work of cohesive failure of the test substance. In this application the means for determining critical pressure further comprises means for measuring the pressure at the moment substantial cohesive failure within the test substance occurs.

In preferred embodiments of the invention the plate or membrane employed remains approximately elastic when subjected to the pressure applied to debond the test substance from the substrate. The plate utilized is preferably a metallic disk. For example, a disk of aluminum that is 0.080 inches in thickness serves as a suitable plate when the test substance employed is a coating, such as paint.

It is quite important for the substrate to be of rigid construction. Otherwise the accuracy of the test will be affected if the substrate deforms. In preparing samples of test substances it is often convenient to apply the test substance to a relatively thin sheet of stainless steel, aluminum, or wood. To ensure that the substrate remains rigid during testing, it is sometimes advisable to provide the system with a rigid substrate reinforcement firmly secured to the substrate on a side thereof opposite the test substance. The substrate reinforcement must have an aperture therethrough that is aligned with the aperture through the substrate. The substrate reinforcement provides enhanced rigidity to the substrate and thereby prevents any errors from occurring due to any deformation of the substrate.

In another broad aspect the invention may be considered to be a method for testing the bond strength of a test substance adhesively bonded to a substrate. The method is comprised of the steps of: applying the test substance to the substrate so as to bond the test substance to the substrate; forming an aperture through the substrate and the test substance; positioning a thin film atop an area of the test substance directly above the aperture, wherein the thin film extends beyond the perimeter of the aperture; forming a groove in the test substance to surround the thin film; bonding a plate to the test substance, thereby encapsulating the film between the test substance and the plate such that the adhesive strength of the bond between the plate and the test substance is greater than the adhesive strength of the bond between the test substance and the substrate; and determining the critical pressure required to create a failure of the test substance in a continuous area of the test substance surrounding the film.

In the implementation of the method the step of determining the critical pressure is preferably performed by: determining the strength of the bond between the test substance and the substrate as a function of the specific work of substantially debonding the test substance from the substrate. The step of determining the critical pressure is further preferably performed by: measuring the pressure at the moment the bond between the test substance and the substrate fails.

As previously noted, the invention is applicable to both a determination of the strength of an adhesive bond between the test substance and the substrate, and also a determination of the strength of the internal cohesive bond created within the test substance itself. In testing the cohesive bond strength within the test substance, the step of determining the critical pressure further comprises the step of determining the internal cohesive strength within the test substance as a function of the specific work of creating substantial cohesive failure within the test substance. In this application the step of determining the critical pressure is further comprised of measuring the pressure at the moment that substantial cohesive failure occurs within the test substance.

Preferably the method of the invention is performed by providing a plate that remains approximately elastic when subjected to the pressure applied to debond the test substance from the substrate or create internal cohesive failure within the test substance.

It is important for the thin film to remain in position atop the test substance directly over the aperture in the substrate. While, with great care, this can be achieved simply by placing the thin film atop the test substance centered above the fluid aperture therethrough such that the periphery of the thin film rests upon the surface of the test substance surrounding the aperture, preferably the thin film is provided with a film adhesive prior to positioning the thin film atop the test substance. The film adhesive lightly bonds the film to the test substance. Also, to guard against inaccuracies caused by any deformation of the substrate, it is sometimes advisable to reinforce the substrate with a reinforcement backing having a backing aperture therethrough aligned with the aperture through the substrate prior to determining the critical pressure.

The invention may be described with greater clarity and particularity by reference to the accompanying drawings.

DESCRIPTION OF THE EMBODIMENTS AND IMPLEMENTATION OF THE METHOD

FIGS. 1–5 illustrate a system for testing the strength of a bond between a test substance 12 and a rigid substrate 14 predrilled with a one-quarter inch diameter aperture 16. The test substance 12 is typically paint, varnish, or some other substance applied in liquid form and cured to form a shell-like coating. By its nature the test substance 12 exerts a substantial adhesive bond with the surface 18 of the substrate 14.

Figure 1:
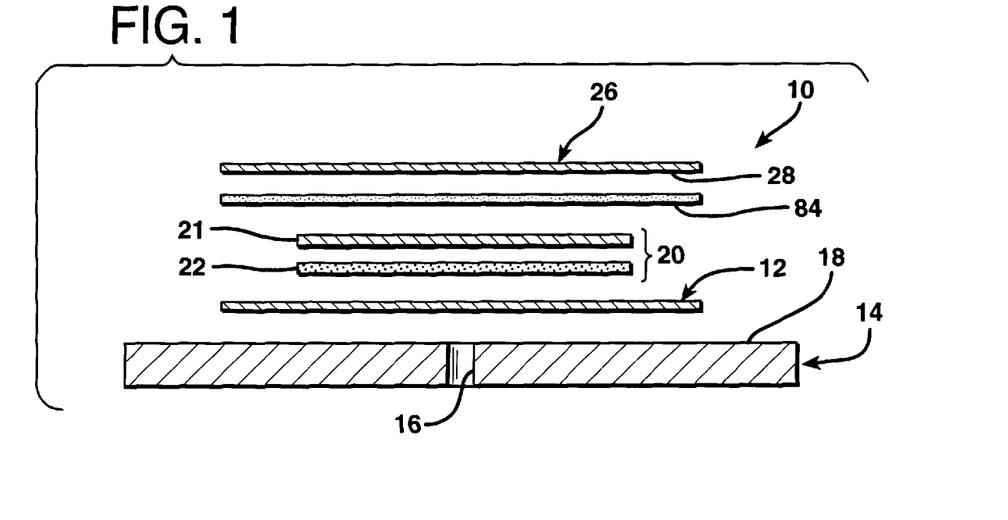
FIG. 1 is an exploded elevational view illustrating the layers and component elements in a test assembly for testing the bonding strength of a coating according to the invention.

The substrate 14 may, for example, be formed of a disk of 6061 aluminum, three inches in diameter and one-quarter of an inch in thickness. Alternatively, the substrate 14 could be formed of stainless steel or any other metal, as well as other materials, such as wood, plastic, or plaster. The choice of the substrate 14 is determined by the substrate of interest to which the test material 12 is likely to be applied on a commercial basis. For example, if it is desired to test the strength of an adhesive bond that a particular paint exhibits with respect to aluminum, an aluminum disk of the type described forms an appropriate substrate 14.

Prior to testing, the substrate 14 is first prepared for bonding. Aluminum substrates 14 are typically prepared for bonding by dipping in a diluted solution of phosphoric acid for about a minute. A stainless steel substrate 14, on the other hand, would typically be dipped in a hot solution of diluted sulfuric acid as set forth in ASTM Standard D-2651, procedure 8, which is a standard recommended practice for preparation of metal surfaces for adhesive bonding.

A coating layer 12 of a test substance such as paint is then applied across the entire substrate 14, covering its entire upper surface 18. The paint layer 12 is then allowed to dry thoroughly. This may take several days.

Once the substrate 14 with the test coating layer of paint 12 thereon has been fabricated and prepared for testing, a thin film disk 20 is positioned thereon. The film disk 20 is provided for covering the portion of the paint layer 12 directly above the aperture 16. The thin film disk 20 is positioned atop the center of the paint layer 12 to be tested and extends beyond the perimeter of the aperture 16.

Figure 2:
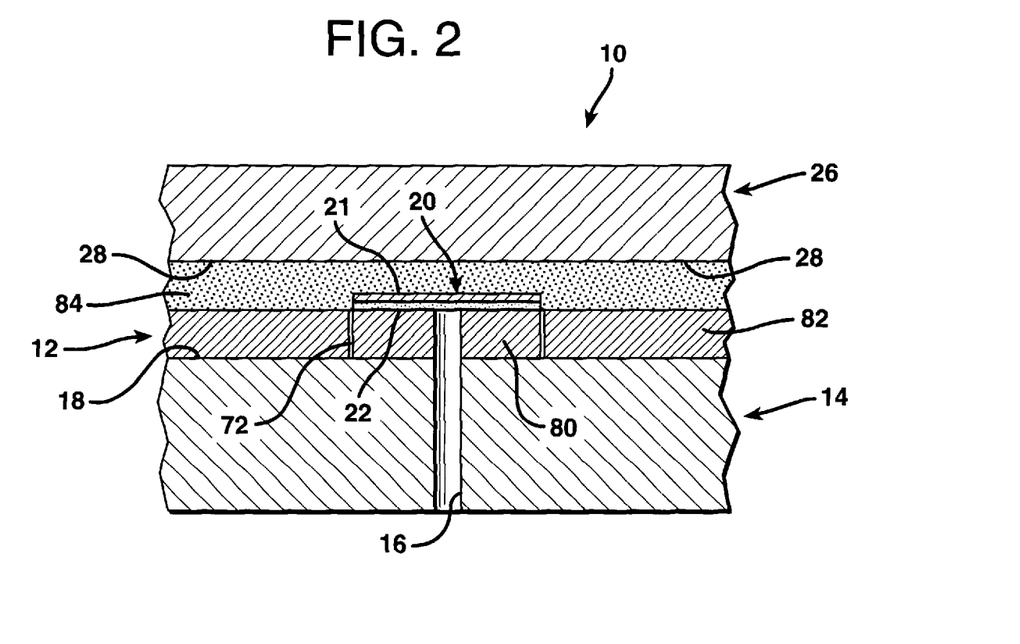
FIG. 2 is a sectional elevational detail illustrating the layers of component elements of FIG. 1 prior to testing.

The thin film 20 may be produced from a composite structure formed by a polyester backing 21, the underside of which has been coated with a weak film adhesive layer indicated at 22, which may be an acrylic adhesive. The thin film disks 20 may be formed as circles die cut from a pressure-sensitive tape and mounted on a strip coated with a release agent prior to use. The composite thickness of the tape formed by the polyester backing 21 and the acrylic adhesive layer 22 on the underside thereof is about 0.0013 inches. Each disk 20 is cut to have a diameter of one and one-half inches. Suitable tapes from which the thin film disks 20 may be fabricated are sold commercially by 3M Company, located in Minneapolis, Minn., as 3M Protective Tapes. One suitable tape is sold as Part No. 1614. Once the thin film disk 20 is centered atop the aperture 16, the film adhesive 22 is pressed into contact with the surface of the paint layer 12 surrounding the aperture 16.

With the thin film disk 20 in position, a circular groove 72 is cut into the paint layer 12 by scoring the paint layer 12 about the perimeter of the thin film patch or disk 20 with a sharp tool, such as a knife or a circular die. The groove 72 is created in order to isolate the central region 80 of the paint layer 12 from the surrounding peripheral region 82 thereof to be tested. Thus, even though irregularities may exist in the central region 80 of the paint layer 12 at the aperture 16, they are of no consequence since they will not affect the force required to create a failure in the bond of the peripheral region 82 of the paint layer 12 to the substrate 14.

A plate 26 is provided and is preferably made of a relative strong material which remains substantially or at least approximately elastic during the test. That is, the plate 26 can withstand the conditions of the test without greatly exceeding its elastic limit. For example, a thin layer of steel, metal foil, or a strong composite material may be utilized as the plate 26. The plate 26 may, for example, be formed of a disk of 7075-T6 aluminum that is two and one-quarter inches in diameter and 0.080 inches in thickness.

The plate 26 is first subjected to the same surface preparation as the substrate 14. The plate 26 is then positioned with a first side 28 thereof facing the paint layer 12 to be tested. An overcoat adhesive layer 84 is applied in liquid form atop the paint layer 12. The adhesive layer 84 should be a very high-strength adhesive. The adhesive layer 84 may, for example, be an adhesive manufactured by Hysol Manufacturing, located in Richmond, Calif., manufacturers adhesive No. 9330 with 0.003 inch diameter glass beads therein.

Once the overcoat adhesive layer 84 has been applied atop the layer of paint 12, the aluminum plate 26 is placed atop the adhesive layer 84 with the surface 18 of the plate 26 in contact therewith. The composite layers shown in the exploded illustration of FIG. 1 are then compressed as depicted in FIG. 2. The overcoat adhesive layer 84 between the underside 28 of the plate 26 bonds the plate 26 to the paint layer 12 to be tested such that the adhesive strength of the bond between the plate 26 and the paint layer 12 being tested is greater than the strength of the bond between the paint layer 12 and the substrate 14.

Curing of the adhesive layer 84 produces the test assembly 10, the central portion of which is shown in detail in FIG. 2. The test assembly 10 is a composite structure formed of several layers including the substrate 14, test coating 12, pressure-sensitive acrylic adhesive 22, polyester backing 21, high strength adhesive layer 84, and the plate 26. The test assembly 10 is then placed in the test fixture 30 illustrated in FIGS. 3 and 4. The test fixture 30, with the test assembly 10 depicted in FIGS. 1 and 2 encased therein, is then used to test the strength of the bond established between the test coating 12 and the substrate 14.

Figure 3:
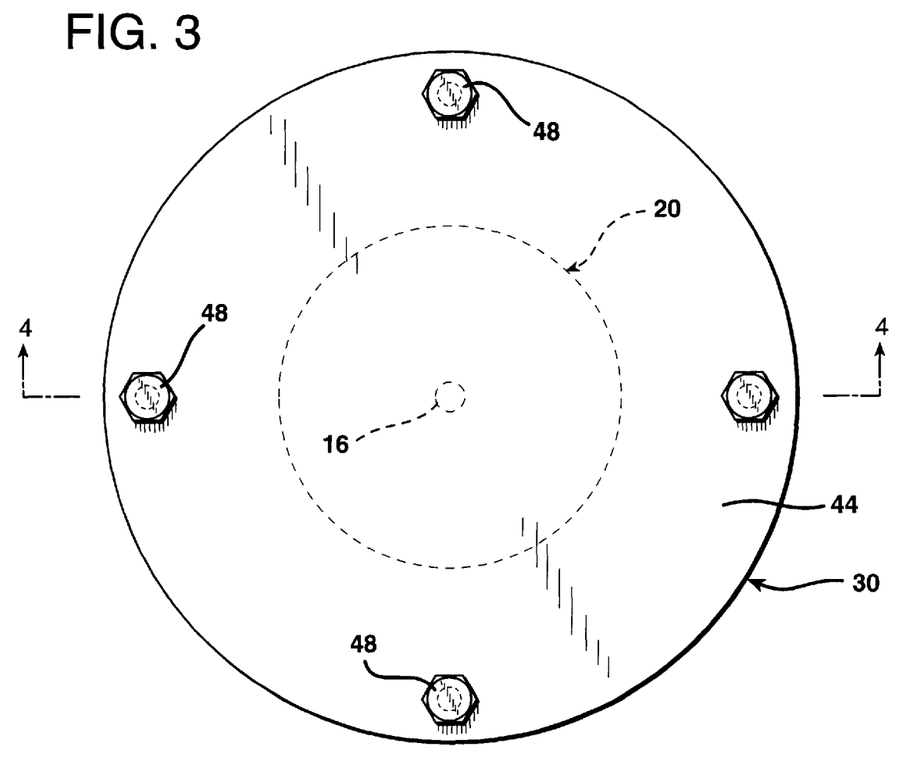
FIG. 3 is a top plan view of a test fixture employed in the test system of the invention.
Figure 4:
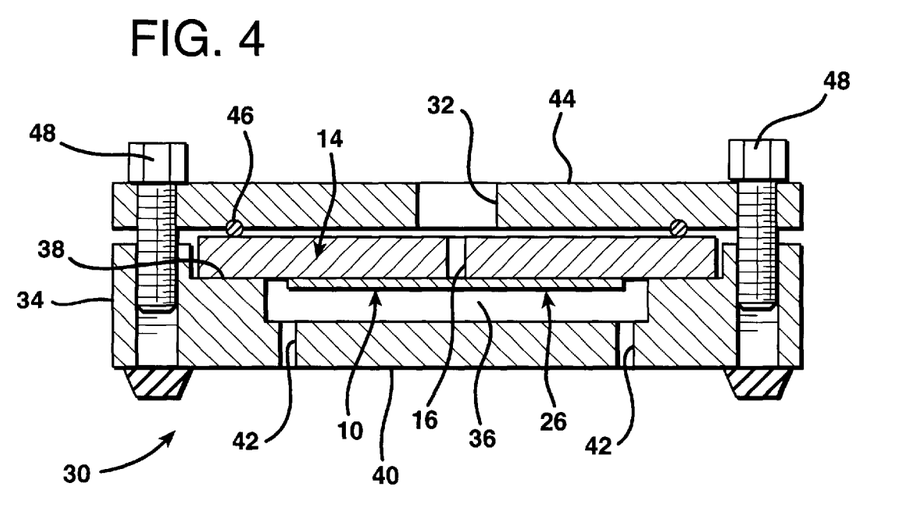
FIG. 4 is a sectional elevational view taken along the line 4—4 of FIG. 3.

The test fixture 30 is illustrated in detail in FIGS. 3 and 4 and is fabricated as a generally disk-shaped or cylindrical-shaped structure. The test fixture 30 employs a steel base 34 shaped generally in the form of a disk-shaped tray. The base 34 is provided with a central cavity 36 therewithin bounded about its outer periphery by an upright annular outer wall forming an annular seating ledge 38, and at its bottom by a floor 40. The floor 40 is provided with a plurality of fluid outlets 42 therethrough.

The test fixture 30 also includes a disk-shaped steel cover 44 in the center of which the central, axial fluid inlet port 32 is defined. The underside of the cover 44 is provided with an annular groove therein adapted to receive the O-ring 46.

The outer wall of the base 34 has four, internally-tapped bores located near its outer periphery and spaced at 90-degree intervals to receive externally threaded cap screws 48. The cover 44 has four peripheral openings therethrough that are aligned with the internally-tapped bores in the wall of the base 34. With the cover 44 removed, the test assembly 10 of FIGS. 1 and 2 is inverted and placed into the cavity 36, with the surface 18 of the substrate 14 resting atop the peripheral ledge 38 defined in the base 34.

With the O-ring 46 in position in the groove of the cover 44, the cover 44 is secured to the base 34 by engaging and tightening all four cap screws 48. The threaded shanks of the cap screws 48 are passed through the four openings defined near the periphery of the cover 44 that are aligned with the tapped bores in the fixture base 34. The threaded shanks of the cap screws 48 are engaged in the tapped bores in the walls of the fixture 34 and tightened to compress the cover 44 toward the bearing ledge 38 of the fixture base 34. Continued tightening of the cap screws 48 causes the substrate 14 to compress the O-ring 46 thereby creating a fluid-tight seal between the surface 17 of the substrate 14 and the cover 44 of the fixture 30. The test assembly 10 is thereupon tightly clamped within the test fixture 30.

Figure 5:
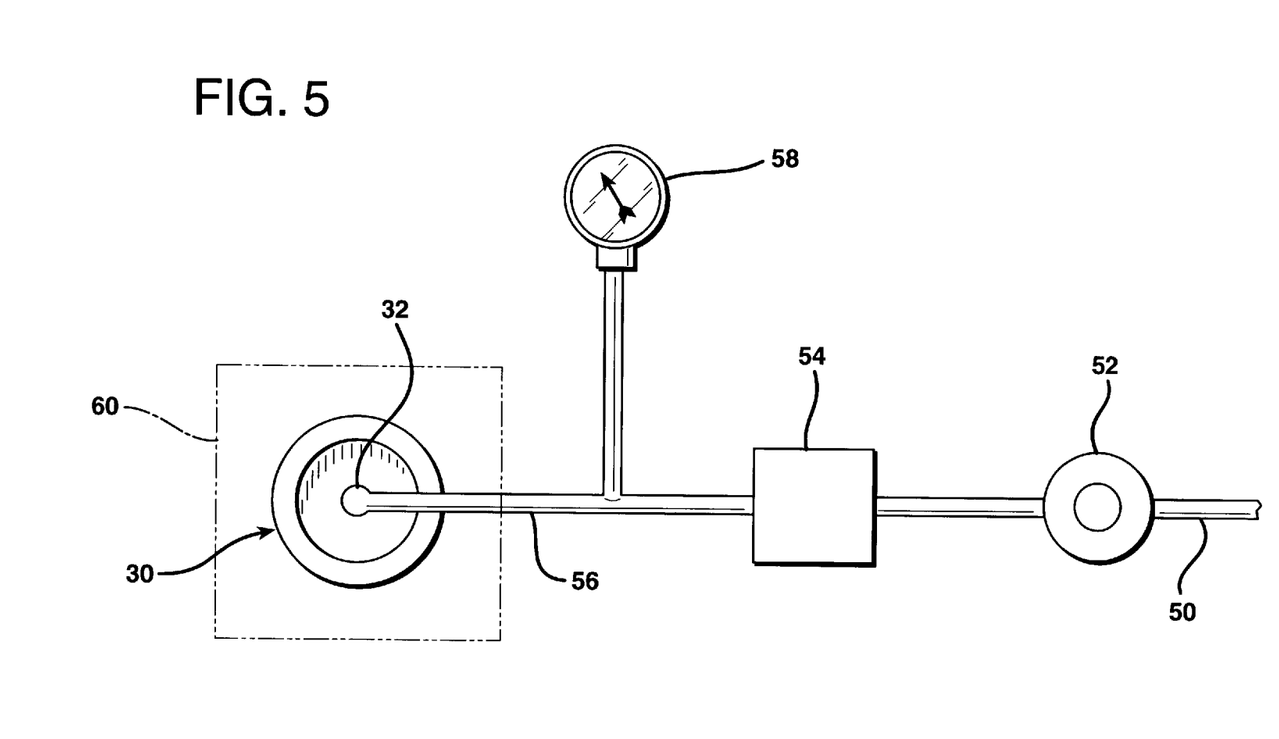
FIG. 5 is a diagrammatic view of a system constructed according to the invention.

The test fixture 30 is then connected to a fluid pressure source, not shown, in the manner depicted in FIG. 5. FIG. 5 illustrates diagrammatically a typical testing system according to the invention in which an inert gas or liquid is applied under pressure to the test fixture 30. The external source of pressurized fluid, such as nitrogen, is provided to line 50. The pressure of the fluid is adjustable by a pressure regulator 52. A valve 54 controls the flow of the fluid to the test fixture 30 through a coupling line 56. The coupling line 56 is coupled to the fluid aperture 16 in the substrate 14 through the pressure inlet port 32. A pressure gauge 58 measures the pressure of the fluid within the test system. The pressure gauge 58 may be a mechanical or digital device, and has the capability of recording maximum pressure measurements and indicates the scale pressure of the highest pressure that is registered within the test fixture 30.

In the operation of the system of the invention the composite structure 10 is enclosed within the test fixture 30 as previously described. Pressurized fluid is supplied to the test fixture 30 and pressure is increased until the test substance, namely the peripheral region 82 of the layer of paint 12, debonds from the substrate 14. The pressure at the moment of debonding is recorded as the critical pressure.

The following formula is used to determine the bonding strength: $G=m\ P^n$, where "G" is the specific work of the debonding, "P" is the critical pressure, and "m" and "n" are constants inherent to the system design. After the system check is completed, it is necessary only to observe the critical pressure. Critical pressure may be taken directly from the pressure gauge 58, and the specific work of debonding may be determined in any system of units, (e.g., English, metric, or SI), using a digital system.

The test fixture 30 may be placed in a chamber 60 during testing to determine the effects of environmental conditions, such as extreme temperatures or corrosive atmospheres, upon the adhesive strength of a material. To further evaluate the effects of a corrosive environment upon adhesive strength, a corrosive gas or liquid may be used as the pressurizing fluid.

The strength of the bond of the pressure-sensitive adhesive layer 22 is quite weak as compared with both the bond formed by the test coating 12 with the upper surface 18 of the substrate 14 and also the bond formed between the plate 26 and the test coating 12. In addition, the adhesive strength of the bond between the plate 26 and the test coating 12 is greater than the strength of the bond between the test coating 12 and the substrate 14.

Figure 6:
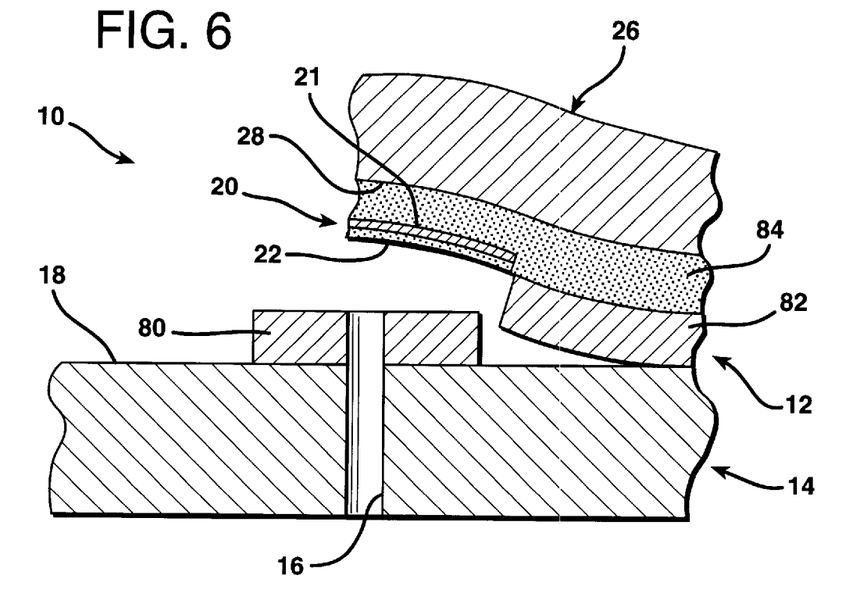
FIG. 6 is a sectional elevational detail illustrating failure of an adhesive bond in determining the adhesive strength of a test substance according to the invention.

The failure of the bond of the test substance may occur as either an adhesive failure or as a cohesive failure. FIG. 6 illustrates the failure of the adhesive bond between the test coating 12 and the substrate 14 when the failure occurs as a separation of the adhesive layer 12 from the substrate 14. Pressure applied through the pressure inlet port 32 leading to the fluid aperture 16 in the substrate 14 readily debonds the central region of the pressure-sensitive adhesive layer 22 from the upper surface of the central region 80 of the test coating 12 and plate 26 deflects above the circular central region 80 until adhesive failure of the bond between the peripheral region 82 of the test coating 12 and the substrate 14 occurs.

The test assembly 10 is depicted at the moment of failure in FIG. 6, during which the region 82 of the paint layer 12 just beyond the groove 72 surrounding the perimeter of the thin film 20 begins to separate from the surface 18 of the substrate 14. Once separation commences, it progresses rapidly radially outwardly until the plate 26, with the annular test coating region 82 still adhesively bonded thereto, pops entirely free of the substrate 14. The plate 26 is constrained in its movement by the floor 40 of the cavity 36, however.

Figure 7:
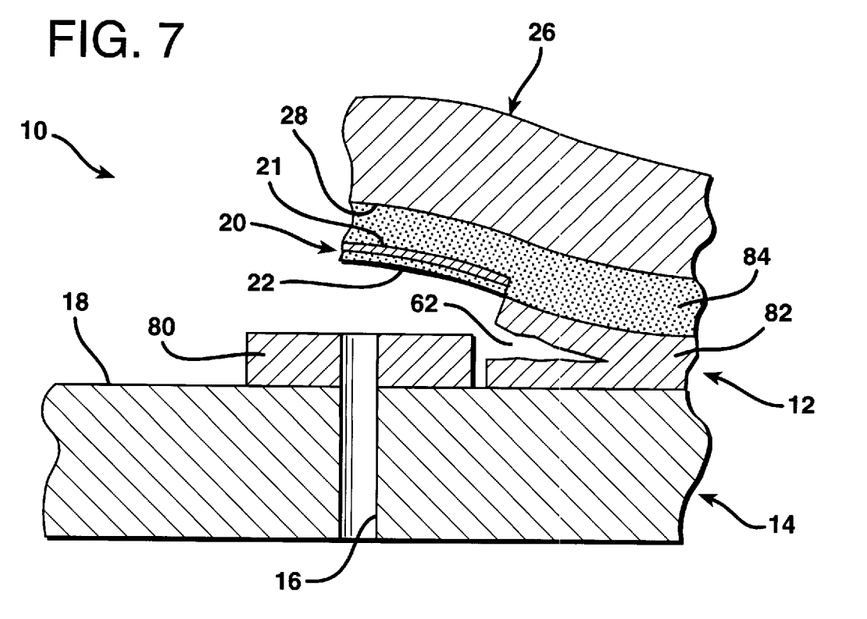
FIG. 7. is a sectional elevational detail illustrating cohesive failure in determining the internal cohesive bonding strength of a test substance according to the invention.

Alternatively, the system may be utilized to test cohesive failure as well. FIG. 7 illustrates the system of the invention at the moment of cohesive failure within the test coating 12. As in the failure of the adhesive bond of the test coating 12, the pressure-sensitive adhesive bond of the pressure-sensitive adhesive layer 22 with the upper surface of the central region 80 of the paint layer 12 fails almost at once so that the pressure does not act to create a failure within the central region 80 of the paint layer 12. Rather, pressure increases until failure occurs due to internal separation within the peripheral region 82 of the test coating 12, indicated generally at 62, as depicted in FIG. 7. That is, a portion of the test coating region 82 of the paint layer 12 remains adhesively secured to the surface 18 of the substrate 14, but the portion immediately adjacent thereto gives way. A fracture thereby forms within the structure of the test coating 12, as depicted at 62.

When cohesive failure occurs as depicted in FIG. 7, the critical pressure registered by the pressure gauge 58 is the pressure required to cause substantial cohesive failure within the test coating 12. In this application the gauge 58 measures the pressure at the moment substantial internal cohesive failure within the test coating 12 occurs. In either mode of failure the plate 26 remains elastic when subjected to the pressure applied to debond the test coating 12 from the substrate 14 or to cause cohesive failure.

In some situations it may prove necessary to reinforce the substrate 14 to ensure that it remains rigid and does not deform before the critical pressure is reached. Such a situation includes the same component substances and layers as the test assembly 10, but in addition includes a "doubler" which is formed of another aluminum disk having a size and construction identical to the substrate 14. This reinforcement disk is constructed and secured to the substrate 14 as described in my prior U.S. application Ser. No. 08/746,496.

The reinforcement disk also has a one-fourth inch diameter aperture drilled through its center. In securing the reinforcement backing to the substrate 14 utilizing the same adhesive substrate that is employed in the adhesive layer 84, care is taken to ensure that the apertures 76 and 16 are in substantial coaxial alignment. The reinforced test assembly is clamped within the test fixture 30 and pressure is applied until the critical pressure is reached in the manner previously described.

Undoubtedly, numerous variations and modifications of the invention will become readily apparent to those familiar with adhesion testing systems. For example, any number of different materials may be employed to form the substrate, the thin film for covering the central region of the test substance above the aperture in the substrate, the test substance itself, the plate and the adhesive that bonds the test substance to the plate. Accordingly, the scope of the invention should not be construed as limited to this specific embodiments of the invention depicted nor the specific implementations of the method described.

I claim:

1. A system for testing the strength of a bond between a test substance and a rigid substrate through which an aperture is defined comprising:

a plate;

an overcoat adhesive layer between the plate and the test substance, wherein the overcoat adhesive layer bonds the plate to the test substance with an adhesive strength greater than the strength of the bond between the test substance and the substrate;

a thin film interposed between the test substance and the overcoat adhesive layer directly above the aperture and extending beyond the perimeter of the aperture and wherein the test substance is scored about the periphery of the thin film;

means for applying increasing pressure through the aperture in the substrate to debond the test substance from the substrate; and means for determining the critical pressure required to substantially debond a continuous periphery of an area in the test substance from the substrate, the critical pressure being directly related to the specific work of debonding.

2. The system of claim 1 wherein the means for determining the critical pressure further comprises;

means for determining the adhesive strength of the bond between the test substance and the substrate directly from the pressure required to cause substantial bond failure as a function of the specific work of debonding the test substance from the substrate; and wherein the means for determining the critical pressure further comprises:

means for measuring the pressure at the moment the bond between the test substance and the substrate fails.

3. The system of claim 1 in which the plate remains elastic when subjected to the pressure applied to debond the test substance from the substrate.

4. The system of claim 1 further comprising an adhesive layer on the underside of the thin film for holding the thin film in position on the test substance.

5. The system of claim 1 wherein the test substance is a coating material bonded to the substrate.

6. The system of claim 5 wherein the coating material is comprised of paint.

7. The system of claim 1 further comprising a rigid substrate reinforcement firmly secured to the substrate on a side thereof opposite the test substance, and wherein the substrate reinforcement has an aperture therethrough aligned with the aperture through the substrate.

8. A system for testing the cohesive strength of a test substance bonded to a rigid substrate through which an aperture is defined comprising:

a plate;

an overcoat adhesive layer bonded to the plate and to the test substance, wherein the overcoat adhesive layer bonds the plate to the test substance with a strength greater than the cohesive strength of the test substance;

a thin film over the test substance interposed between the test substance and the overcoat adhesive layer directly above the aperture and extending beyond the perimeter of the aperture, and wherein a groove is formed in the test substance about the periphery of the thin film to avoid the application of pressure to the portion of the test substance directly beneath the thin film;

means for applying increasing pressure through the aperture in the substrate to cause cohesive failure in the test substance; and means for determining the critical pressure required to cause cohesive failure around a continuous periphery of an area in the test substance, the critical pressure being directly related to the specific work of cohesive failure.

9. The system of claim 8 wherein the means for determining the critical pressure further comprises:

means for determining the internal cohesive strength of the test substance directly from the pressure required to cause substantial cohesive failure therewithin, and wherein the means for determining critical pressure further comprises:

means for measuring the pressure at the moment substantial cohesive failure within the test substance occurs.

10. The system of claim 8 in which the plate remains elastic when subjected to the pressure applied to debond the test substance from the substrate.

11. The system of claim 8 further comprising adhesive on the underside of the thin film for bonding the thin film to the test substance.

12. The system of claim 8 wherein the test substance is a coating material bonded to the substrate.

13. The system of claim 12 wherein the coating material is comprised of paint.

14. The system of claim 8 further comprising a rigid substrate reinforcement firmly secured to the substrate on a side thereof opposite the test substance, and wherein the substrate reinforcement has an aperture therethrough aligned with the aperture through the substrate.

15. A method for testing the strength of a test substance bonded to a substrate comprising the steps of:

applying the test substance to the substrate so as to bond the test substance to the substrate;

forming an aperture through the substrate and the test substance;

positioning a thin film patch atop an area of the test substance directly above the aperture, wherein the thin film patch extends beyond the perimeter of the aperture;

forming a groove in the test substance to surround the thin film patch;

bonding a plate to the test substance, thereby encapsulating the film between the test substance and the plate such that the adhesive strength of the bond between the plate and the test substance is greater than the adhesive strength of the bond between the test substance and the substrate; and determining the critical pressure required to create a failure of the test substance in a continuous area of the test substance surrounding the film patch.

16. The method of claim 15 wherein the step of determining the critical pressure further comprises:

determining the strength of the bond between the test substance and the substrate as a function of the specific work of substantially debonding the test substance from the substrate, by measuring the pressure at the moment the bond between the test substance and the substrate fails.

17. The method of claim 15 wherein the step of determining the critical pressure further comprises the step of:

determining the internal cohesive strength within the test substance as a function of the specific work of creating substantial cohesive failure within the test substance by measuring the pressure at the moment that substantial cohesive failure occurs within the test substance.

18. The method of claim 15 further comprising the step of:

bonding the plate to the test substance utilizing an overcoating adhesive.

19. The method of claim 15 further comprising holding the thin film patch in position above the aperture by first coating the underside of the thin film patch with a film adhesive that bonds the film patch to the test substance prior to positioning the thin film patch atop the test substance.

20. The method of claim 15 wherein the test substance is paint.

* * * * *